United States Patent
Tafas et al.

(10) Patent No.: US 7,330,309 B2
(45) Date of Patent: *Feb. 12, 2008

(54) SYSTEM AND METHOD FOR INCREASING THE CONTRAST OF AN IMAGE PRODUCED BY AN EPIFLUORESCENCE MICROSCOPE

(75) Inventors: Triantafyllos Tafas, Rocky Hill, CT (US); Petros Tsipouras, Madison, CT (US)

(73) Assignee: Ikonisys, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/225,460

(22) Filed: Sep. 13, 2005

(65) Prior Publication Data

US 2006/0056016 A1    Mar. 16, 2006

Related U.S. Application Data

(63) Continuation of application No. 10/102,500, filed on Mar. 19, 2002, now Pat. No. 6,956,695.

(60) Provisional application No. 60/276,906, filed on Mar. 19, 2001.

(51) Int. Cl.
*G02B 21/34* (2006.01)

(52) U.S. Cl. .................... 359/396; 359/359

(58) Field of Classification Search .............. None
See application file for complete search history.

(56) References Cited

U.S. PATENT DOCUMENTS

| | | | |
|---|---|---|---|
| 3,764,772 A | 10/1973 | Matuschek | |
| 3,879,706 A | 4/1975 | Favier et al. | |
| 4,122,518 A | 10/1978 | Castleman et al. | |
| 4,175,860 A | 11/1979 | Bacus | |
| 4,400,370 A | 8/1983 | Kass | |
| 4,523,278 A | 6/1985 | Reinhardt et al. | |
| 4,615,878 A | 10/1986 | Kass | |
| 4,656,594 A | 4/1987 | Ledley | |
| 4,675,286 A | 6/1987 | Calenoff | |
| 4,711,955 A | 12/1987 | Ward et al. | |
| 4,741,043 A | 4/1988 | Bacus | |
| 4,780,405 A | 10/1988 | Kaiser et al. | |

(Continued)

FOREIGN PATENT DOCUMENTS

EP    0 070 687 B1    7/1982

(Continued)

OTHER PUBLICATIONS

The Lancet, Semiquantitative detection of Down's syndrome with PCR, vol. 40, Sept. 5, 1992, pp. 620-621.

(Continued)

*Primary Examiner*—Arnel Lavarias
(74) *Attorney, Agent, or Firm*—Kelley Drye & Warren LLP

(57) ABSTRACT

The contrast of an image produced by epifluorescence microscopy may be increased by placing a high-pass dichroic reflecting film behind the sample. The reflecting film reflects the emission light emitted by the fluorescent tags in the sample back through the objective lens while allowing the shorter wavelength excitation light to pass through the sample holder.

13 Claims, 4 Drawing Sheets

U.S. PATENT DOCUMENTS

| | | | |
|---|---|---|---|
| 4,833,251 A | 5/1989 | Musso et al. |
| 4,874,693 A | 10/1989 | Bogart |
| 4,900,934 A | 2/1990 | Peeters et al. |
| 4,910,300 A | 3/1990 | Urdea et al. |
| 4,965,725 A | 10/1990 | Rutenberg |
| 4,983,044 A | 1/1991 | Schweber |
| 4,996,040 A | 2/1991 | Kass |
| 5,000,192 A | 3/1991 | Sealfon |
| 5,004,681 A | 4/1991 | Boyse et al. |
| 5,008,185 A | 4/1991 | Bacus |
| 5,018,209 A | 5/1991 | Bacus |
| 5,041,733 A | 8/1991 | Noguchi et al. |
| 5,073,857 A | 12/1991 | Peters et al. |
| 5,077,806 A | 12/1991 | Peters et al. |
| 5,109,429 A | 4/1992 | Bacus et al. |
| 5,130,446 A | 7/1992 | Musso et al. |
| 5,153,117 A | 10/1992 | Simons |
| 5,175,269 A | 12/1992 | Stavrianopoulos |
| 5,192,553 A | 3/1993 | Boyse et al. |
| 5,204,884 A | 4/1993 | Leary et al. |
| 5,225,326 A | 7/1993 | Bresser et al. |
| 5,241,060 A | 8/1993 | Engelhardt et al. |
| 5,252,487 A | 10/1993 | Bacus et al. |
| 5,287,272 A | 2/1994 | Rutenberg et al. |
| 5,328,824 A | 7/1994 | Ward et al. |
| 5,447,841 A | 9/1995 | Gray et al. |
| 5,491,224 A | 2/1996 | Bittner et al. |
| 5,629,147 A | 5/1997 | Asgari et al. |
| 5,714,325 A | 2/1998 | Bianchi |
| 5,732,158 A | 3/1998 | Jaenisch |
| 5,766,784 A | 6/1998 | Baskaran et al. |
| 5,776,688 A | 7/1998 | Bittner et al. |
| 5,787,201 A | 7/1998 | Nelson et al. |
| 5,809,169 A | 9/1998 | Rezzouk et al. |
| 5,859,919 A | 1/1999 | Holland et al. |
| 6,088,097 A | 7/2000 | Uhl |
| 6,094,274 A | 7/2000 | Yokoi |
| 6,210,889 B1 | 4/2001 | Drouin et al. |
| 6,277,569 B1 | 8/2001 | Bittner et al. |
| 6,388,788 B1 | 5/2002 | Harris et al. |
| 6,391,593 B1 | 5/2002 | Weston et al. |
| 2001/0028497 A1 | 10/2001 | Uhl |

FOREIGN PATENT DOCUMENTS

| | | |
|---|---|---|
| EP | A-0421736 | 4/1991 |
| EP | 0 512 965 B1 | 11/1992 |
| JP | 04151614 A | 5/1992 |
| JP | 08082747 A | 3/1996 |
| JP | 9-292572 | 11/1997 |
| JP | 11072435 A | 3/1999 |
| WO | WO 86/06726 | 11/1986 |
| WO | WO 90/05789 | 5/1990 |
| WO | A-92/13308 | 8/1992 |
| WO | WO 93/06245 | 4/1993 |
| WO | WO 93/21345 | 10/1993 |
| WO | WO 94/02646 | 2/1994 |
| WO | WO 94/02829 | 2/1994 |
| WO | WO 94/02830 | 2/1994 |
| WO | WO 01/37192 | 5/2001 |
| WO | WO 02/074055 | 9/2002 |

OTHER PUBLICATIONS

Prenatal Diagnosis, First-Trimester Maternal Serum Biochemical Indicators in Down Syndrome, vol. 10, 1990, pp. 245-251.

Prenatal Diagnosis, vol. 11, Cu/Zn Superoxide Dismutase Quantification from Fetal Erythrocytes-An Efficient Confirmatory Test for Down's Syndrome After Maternal Serum Screening and Sonographic Investigations, 1991, pp. 295-303.

Lichter P, Boyle Al, Cremer T, Ward DC (1991) Analysis of Genes and Chromosomes by Nonisotopic in situ Hybridization. Genet Anal Techn Appl 8 (1): 24-35.

Du Manoir S, Speicher MR, Joos S, et al (1993) Detection of Complete and Partial Chromosome Gains and Losses by Comperative Genomic in situ Hybridization. Hum Genet 90: 590-610.

Lockett et al., Analytical and Quantitative Cytology and Histology, vol. 13, No. 1, pp. 29-44, Feb. 1991.

Lockett et al., Quantitative Precision of an Automated Fluorescence-Based Image Cytometer, vol. 14, No. 3, pp. 187-202, Jun. 1992.

Lockett et al., Automated Image-Based Cytometry with Fluorescence-Stained Specimens, Bio Techniques, vol. 10, No. 4, pp. 514-519, 1991.

Poon, et al., Automated Image Detection and Segmentation in Blood Smears, Cytometry, vol. 13, pp. 766-774, 1992.

Neuromedical Systems, Inc., The breakthrough in automated Pap Smear Screening, 1989-1990, 5 pages.

Parthenis et al., Blood analysis using black and white digital images, J. Biomed, Eng., vol. 14, pp. 287-292, Jul. 1992.

Abstract: Sigma Diagnostics, Alkaline Phosphatase, Leukocyte, Procedure No. 86, Oct. 1990, 4 pages.

Media Cybernetics, Image-Pro Plus Manual, pp. 6-12-6-13, 6-39-8-43, A-21-A-23.

Clinical Chemistry, Measuring Unconjugated Estriol in Maternal Serum to Screen For Fetal Down Syndrome, vol. 38, No. 9, 1992, pp. 1687-1689.

The Lancet, Urea-Resistant Neutrophil Alkaline Phosphatase in Mothers with Trisomy 21 Pregnancy, Oct. 1, 1983, pp. 799-800.

International Search Report PCT/US02/08646, Jul. 2002.

SYSTEM AND METHOD FOR INCREASING THE CONTRAST OF AN IMAGE PRODUCED BY AN EPIFLUORESCENCE MICROSCOPE

CROSS-REFERENCE TO RELATED APPLICATIONS

This is a continuation application of U.S. patent application Ser. No. 10/102,500, filed Mar. 19, 2002 now U.S. Pat. No. 6,956,695, which claims priority of U.S. Provisional Application No. 60/276,906, filed Mar. 19, 2001, the entire contents of which are incorporated herein by reference in their entirety.

FIELD OF THE INVENTION

The present invention relates to microscope slides and the like for use in epifluorescence microscopy of biological specimens.

BACKGROUND OF THE INVENTION

Citation or identification of any reference in this section or any section of this application shall not be construed as an admission that such reference is available as prior art to the present invention.

An epifluorescence microscope is similar to a conventional reflecting optical microscope in that both microscopes illuminate the sample and produce a magnified image of the sample. An epifluorescence microscope, however, uses the emitted fluorescent light to form an image whereas a conventional reflecting optical microscope uses the scattered illumination light to form an image. The epifluorescent microscope uses a higher intensity illumination, or excitation, light than a conventional microscope. The higher intensity excitation light is needed to excite a fluorescent molecule In the sample thereby causing the fluorescent molecule to emit fluorescent light. The excitation light has a higher energy, or shorter wavelength, than the emitted light. The epifluorescence microscope uses the emitted light to produce a magnified image of the sample. The advantage of an epifluorescence microscope is that the sample may be prepared such that the fluorescent molecules are preferentially attached to the biological structures of interest thereby producing an image of the biological structures of interest.

A common problem in epifluorescence microscopy is the low contrast, or low signal-to-noise (S/N) ratio, of the fluorescent image. This is due to the low intensity of the emitted light compared to the high intensity of the excitation light. A dichroic mirror is usually used to reduce the scattered excitation light before the image is viewed or recorded.

The dichroic mirror is only partially effective in removing the excitation light from the emitted light so other measures must be taken to increase the S/N ratio of the fluorescent image. In order to assist in the discussion of the other approaches to increasing the S/N ratio of the fluorescent image, reference to FIG. 1 is helpful.

FIG. 1 illustrates the optical path and components of a typical epifluorescence microscope. A sample 100 is placed on a sample holder 105, which is normally a microscope slide. The sample is prepared prior to being placed on the holder 105 with fluorescent tags that bind to the biological structures of interest. The fluorescent tags may be a single type of fluorescent tag that binds to a particular biological structure or may be a mixture of several fluorescent tag types with each tag type binding to a different biological structure. The sample 100 is illuminated by a light source 110 that produces the excitation light with sufficient intensity to cause the tags to emit fluorescent light. The excitation light generated by the light source 110 follows a path 115 through an excitation filter 120 that acts as a band-pass filter allowing only a narrow range of frequencies to pass through the excitation filter 120. The excitation filter 120 is chosen to allow only the light of a frequency that will cause the tags to fluoresce. The excitation light is reflected by a dichroic mirror 130 into the objective lens 140 of the microscope following path 125. A dichroic mirror separates the excitation light from the emission light, in this example, by reflecting the excitation light while transmitting the emission light. The excitation light propagates through the objective lens 140 and illuminates the sample 100 and excites the tags in the sample to emit fluorescent light, also referred to as emission light. The emission light propagates along path 125 in the opposite direction as the excitation light. The emission light passes through the objective lens 140 and through the dichroic mirror 130 and continues along path 135 through an emission filter 150. The emission filter 150 is selected to allow only light matching the frequency of the emission light to pass through the filter. The emission filter 150 may be a band-pass fitter, or a long-pass filter that allows the longer wavelength emission light to pass through while stopping the shorter wavelength excitation light. After filtering by the emission filter 150, the emission light is formed into an image by an imaging lens 160. If the emission filter 150 is perfectly efficient in removing all but the emission light, the magnified fluorescent image would have a very high contrast and S/N ratio. Unfortunately, emission filters are not perfectly efficient so a small amount of excitation light is transmitted though the emission filters. Because the intensity of the excitation light is very high, the small fraction of excitation light that passes through the emission filter is sufficient to severely degrade the contrast of the fluorescent image. In addition, the excitation frequency is usually very close to the emission frequency of the fluorescent tag molecule. The closeness of the two frequencies adds a further requirement on the emission filter that the filter have a very steep adsorption edge between the emission frequency and excitation frequency.

U.S. Pat. No. 6,094,274 issued on Jul. 25, 2000 to Yokoi teaches the use of two interference films as an emission filter. The two interference films act to sharpen the adsorption edge between the emission frequency and excitation frequency. The sharp adsorption edge blocks more of the excitation light while transmitting more of the emission light to the imaging lens.

Another approach to increasing the S/N ratio of a fluorescent image is disclosed in Japanese Application Publication No. 9-292572 by Sudo, et al. published on Nov. 11, 1997 (hereinafter referred to as "Sudo"). Sudo discloses the use of a mirror behind the sample that reflects the excitation light back through the sample. The reflected excitation light approximately doubles the excitation light seen by the sample and therefore approximately doubles the amount of emission light given off by the sample. A portion of the reflected excitation light will, however, also pass through the dichroic mirror and emission filter adding to the "noise" of the higher emission signal. In addition, the increased illumination of the sample from the reflected excitation light increases the bleaching effect on the tagged sample. Bleaching occurs when the fluorescent tag molecules emit decreasing amounts of fluorescent light as the molecules are illuminated by the excitation light. For example, a fluorescent tag molecule will emit less than 10% of its emission intensity after only a minute of being illuminated by the excitation light. As the intensity of the excitation light increases the bleaching rate increases thereby decreasing the emission light and reducing the contrast of the fluorescent image.

Therefore, there still remains a need to provide a microscope system capable of producing a high contrast fluorescent image while reducing unnecessary bleaching of the sample.

SUMMARY OF THE INVENTION

One aspect of the present invention is directed to an epifluorescence microscope for imaging a biological sample having fluorescent tag molecules, the tag molecules emitting an emission light at an emission frequency when illuminated by an excitation light having an excitation frequency, the microscope comprising: an excitation light source generating an excitation light; a first dichroic mirror reflecting the excitation light; an objective lens disposed to receive the excitation light reflected by the dichroic mirror and to illuminate the sample with the excitation light; an imaging lens disposed to receive emission light from the sample through the objective lens and first dichroic mirror; and a dichroic sample reflector disposed behind the sample reflecting the emission light back through the sample, objective lens, first dichroic mirror and imaging lens, while transmitting the excitation light through the reflector.

Another aspect of the present invention is directed to a sample holder for supporting a sample for epifluorescence microscopy, the sample emitting an emission light when illuminated by an excitation light, the sample holder comprising a base and a dichroic reflector disposed on the base, wherein the dichroic reflector reflects the emission light emitted by the sample while transmitting the excitation light illuminating the sample.

Another aspect of the present invention is directed to a microscope slide for supporting a sample, the slide comprising a top surface and an infra-red reflecting film deposited on the top surface, the film directly supporting the sample.

Another aspect of the present invention is directed to a sample holder holding a sample for an epifluorescence microscope, the sample emitting an emission light when illuminated by an excitation light, the sample holder comprising: a base supporting the sample; and a sample reflector disposed on the base between the sample and base, wherein the reflector reflects the emission light emitted by the sample while transmitting the excitation light illuminating the sample, wherein the sample reflector is concave having a focal point disposed in the sample. Another aspect of the present invention is directed to a sample holder for supporting a sample emitting an emission light when illuminated by an excitation light, the sample holder comprising: a top surface for directly supporting a sample, the top surface having an infra-red reflecting film deposited on the top surface; and a bottom surface having a dichroic film deposited on the bottom surface, the dichroic film reflecting emission light and transmitting excitation light.

Another aspect of the present invention is directed to a sample holder for supporting a sample emitting an emission light when illuminated by an excitation light, the sample holder comprising: a top surface for directly supporting a sample; and a dichroic film deposited on the top surface, the dichroic film transmitting excitation light and reflecting emission light.

Another aspect of the present invention is directed to a method for increasing the contrast of an image produced by an epifluorescence microscope of a sample emitting an emission light when illuminated by an excitation light comprising the steps of: illuminating the sample with the excitation light; collecting a first portion of the emission light; reflecting a second portion of the emission light; collecting the reflected portion of the emission light; and producing an image using the collected first portion of the emission light and the collected reflected portion of the emission light.

BRIEF DESCRIPTION OF THE DRAWINGS

The present invention may be understood more fully by reference to the following detailed description of the preferred embodiments of the present invention, illustrative examples of specific embodiments of the invention and the appended figures in which.

DETAILED DESCRIPTION OF THE PREFERRED EMBODIMENTS

Figure 1:
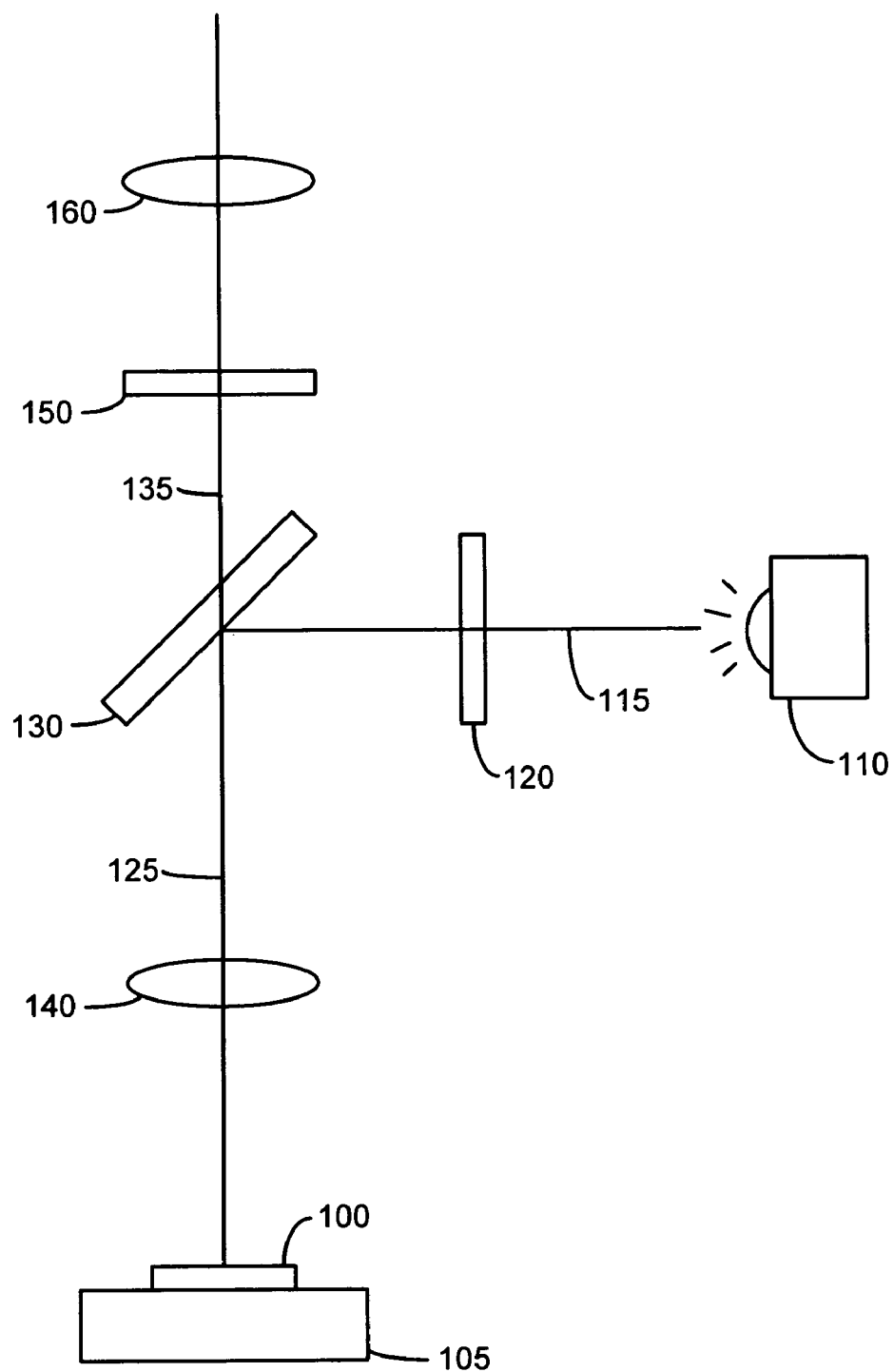
FIG. 1 is a view of a conventional epifluorescence microscope.
Figure 2:
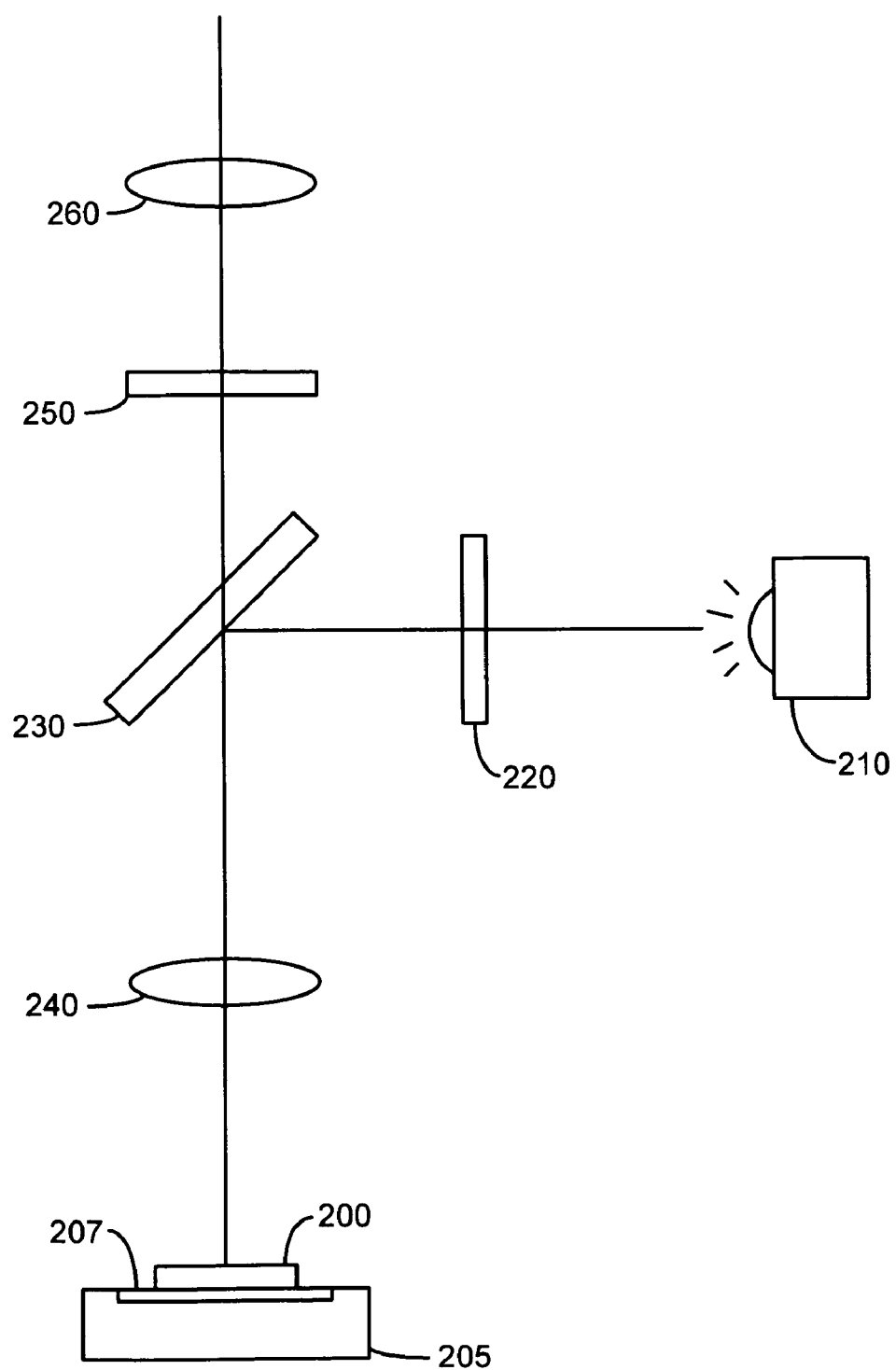
FIG. 2 is a view of an embodiment of the present invention.

FIG. 2 is a view of an embodiment of the present invention. Excitation light generated by a light source 210 is filtered by an excitation filter 220. The excitation filter 220 is preferably a band-pass filter allowing excitation frequencies matched to the fluorescent tags in the sample to pass through while absorbing the rest. The excitation light is redirected by reflection from a dichroic mirror 230 through an objective lens 240 to illuminate a sample 200 having fluorescent tag molecules. The excitation light causes the fluorescent tag molecules to emit fluorescent light. The fluorescent light emitted by the tag molecules is collected by the objective lens 240 and is transmitted through the dichroic mirror 230. The dichroic mirror 230 is selected to reflect the excitation light emitted by the light source 210 toward the sample 200 while transmitting the emission light emitted by the sample through the dichroic mirror. The emission light is filtered by an emission filter 250 to remove extraneous light such as scattered excitation light. The emission light is formed into an image by an imaging lens 260. The details of mounting and aligning the optical elements described above are known to one of ordinary skill in the optical microscopy art and are therefore not discussed.

The sample 200 is supported by a sample holder 205. The sample holder 205 includes a sample reflector 207 positioned directly behind the sample 200. It is understood that the term "behind" is relative to the direction of the incident excitation light. The sample reflector 207, in a preferred embodiment, is a dichroic mirror selected to reflect the emission light while transmitting the excitation light.

Figure 3:
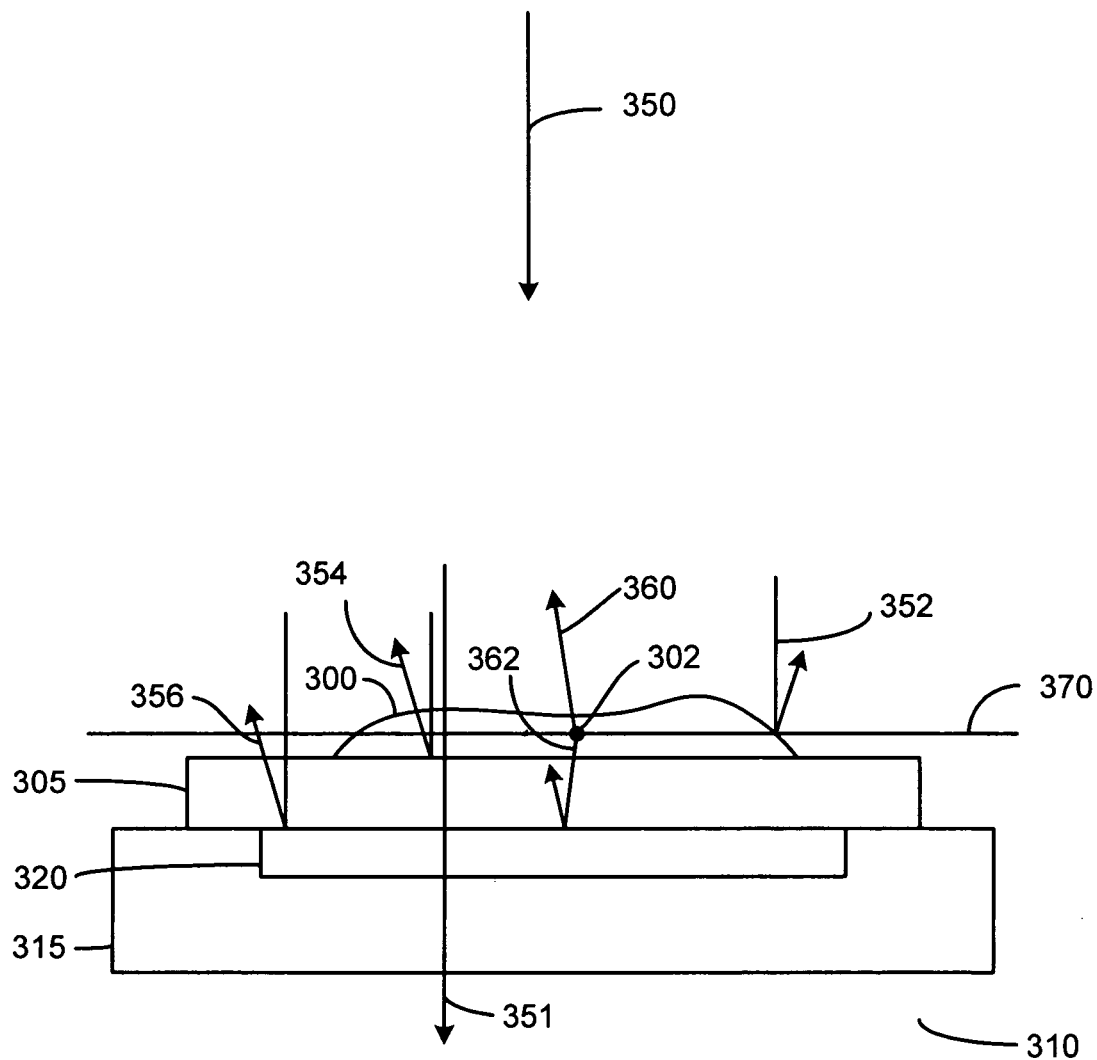
FIG. 3 is a detail view of the sample holder of the embodiment shown in FIG. 2.

FIG. 3 is a detail view of the sample holder 205 and sample reflector 207. A sample 300 such as a blood or cell smear is placed on a sample support 305 such as a glass slide. The sample is treated with a fluorescent tag that preferentially adsorbs to the biological structures of interest. The sample 300 and sample support 305 are supported by a sample holder 310. The sample holder 310 has a base 315 supporting a reflector 320 that, in turn, supports the glass slide 305 and sample 300.

Excitation light 350 illuminates the sample 300 and interacts with the sample 300, sample support 305 and reflector 320. For example, the excitation light 350 may be back-scattered from the sample, shown as ray 352, or may be back-scattered from the sample support 305, shown as ray 354, or may be backscattered from the reflector, shown as ray 356. Some of the back-scattered light 352 354 356 is collected by the objective lens (not shown) and transmitted through to the imaging lens. The back-scattered light 352 354 356 collected by the imaging lens contributes to the background noise level of the image and therefore reduces the S/N ratio of the image.

A small fraction of the excitation light 350 interacts with the fluorescent tags 302 causing the fluorescent tags 302 to emit fluorescent light 360 362. Some of the emission light 360 is collected by the objective lens and imaged by the imaging lens thereby forming the image of the biological structures of interest. Less than one-half of the emission light 360 362 is directly collected by the objective lens because at least one-half of the emission light is emitted in a direction away from the objective lens as represented by ray 362.

In a preferred embodiment, the reflector 320 is a dichroic mirror that allows the short wave-length excitation light 351 to pass through the mirror 320 while reflecting the longer wave-length emission light 362. Selection of the reflector 320 to match the excitation and emission frequencies of the specific fluorescent tag molecule used to prepare the sample is well known to one of ordinary skill in the fluorescent microscopy art.

The novel feature of the reflector 320 is that, unlike the dichroic mirror commonly used in typical epifluorescent microscopes, the reflector 320 reflects the emission light instead of the excitation light. In the preferred embodiment, the reflector 320 transmits or absorbs most of the excitation light 350 and therefore reduces the amount of back-scattered excitation light 356 that may be collected by the objective lens. Reducing the amount of back-scattered excitation light 356 also reduces the noise in the image and results in a higher contrast image of the sample. In addition, the reflected emission light 362 may be collected by the objective lens and contribute to the "signal portion" of the image and thereby create a higher contrast image.

The reflected emission light 362 is reflected from the surface of the reflector 320. The reflector surface is behind, with respect to the direction of the excitation light, the tag molecule in the sample and therefore will not be in the same focal plane 370 as the sample. The resulting image will have a higher intensity due to the reflected emission light but will have a lower resolution due to the spatial displacement of the reflector surface with respect to the plane of the sample. In many situations, the higher intensity image is more important than the slight loss of resolution. For example, if the emission light is used to detect the presence of a rare cell in a sample, a brighter image is preferred because a bright image is easier to detect. The slight loss in resolution in this example is not as important because the detection of the rare cell depends primarily on image brightness, not image resolution.

In another embodiment of the present invention, the sample is placed directly on the reflector 320. Placing the sample directly on the reflector 320 eliminates the need for a sample support 305 and reduces the distance between the plane of the reflector and the plane of the sample 370 thereby reducing the focal mismatch between the image formed by the emission light collected directly from the sample and the image formed by the reflected emission light 362.

The reflection surface may also be used as a reference plane for automatically focusing the image using laser tracking such as the Teletrac LTAF8000 series Laser Tracking Autofocus from Axsys Technologies of Rocky Hill, Conn. In typical auto-focusing methods, the image is focused based on the reflected light from a surface, usually a cover slide. In typical laser autofocusing systems, the frequency of the laser light is usually in the infrared portion of the spectrum and has a longer wavelength than the light emitted by the fluorescent tags. The amount of reflected light is usually less than about 5% of the incident light. The small signal strength of the reflected light causes the microscope to lose focus if the sample is perturbed. In an embodiment where the reflector acts as a high-pass filter allowing the higher frequency excitation light through the filter while reflecting the lower frequency emission and autofocusing light back through the objective lens. Although the reflector may not reflect all of the infra-red focusing light, a sufficient amount of focusing light will be reflected for the laser auto-focus system to maintain focus on the top surface of the reflector.

Figure 4:
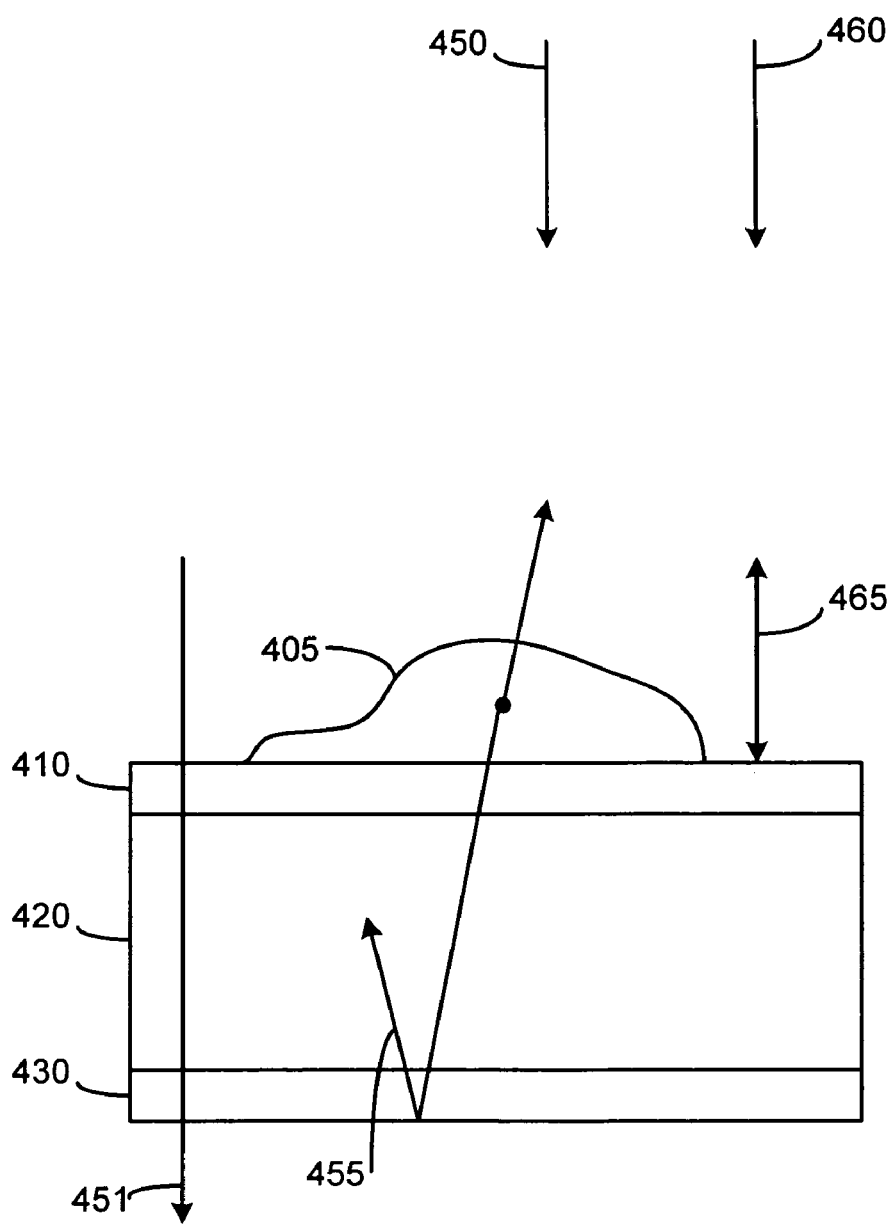
FIG. 4 is a view of another embodiment of the present invention.

FIG. 4 is a side view of another embodiment of the present invention. An infra-red reflecting film 410 is deposited on the top surface of a sample support 420 and a dichroic film 430 reflecting emission light while transmitting excitation light is deposited on the bottom surface of the sample support. The sample support may be a single-use disposable glass slide. The sample 405 is placed directly on the infra-red reflector 410 and illuminated by both the excitation light 450 and a focusing beam 460. The focusing beam 460 is preferably an infra-red beam, characterized by a wavelength between 700-800 nm, that is part of a laser auto-focus system such as the one described above. The focusing beam 460 is reflected (indicated by ray 465) by the infra-red reflecting film 410 back to the laser auto-focus system that automatically focuses the microscope on the infra-red reflecting film 410. In most situations, the biological structures of interest usually settle onto the surface of the infra-red reflecting film 410. Therefore, focusing on the reflecting film 410 will likely bring the biological structures of interest into focus. The dichroic film 430 on the bottom surface of the sample support 420 will reflect the emission light (indicated by ray 455) back through the sample for collection by the objective lens while transmitting or absorbing the excitation light (indicated by ray 451).

In a preferred embodiment, the infra-red reflecting film 410 is metal film, such as for example titanium, between 0.6-90 nm. The metal film may be deposited using any of the known techniques for depositing thin films such as physical deposition. In a preferred embodiment, magnetron sputtering may be used to apply the infra-red reflecting film to the glass slide. The sputtering composition, in a preferred embodiment, is substantially titanium with impurities such as carbon, nitrogen, iron, oxygen, and hydrogen cumulatively comprising less than 1% of the sputtering composition. Other sputtering compositions comprising metals different than titanium may be used to form the metal film.

The selection of the sputtering composition and film thickness may be determined by one of skill in the art by measuring the intensity of the reflected auto-focus beam from the reflecting film. In one embodiment of the present invention, the thickness and composition of the film is adjusted to reflect between 4-8% of the incident infra-red auto-focus beam. In a preferred embodiment, the thickness and composition of the film is adjusted to reflect between 5.5-7% of the incident auto-focus beam.

In other situations, however, a high contrast, high resolution image is preferred. In another embodiment of the present invention, the reflector is shaped into a concave surface having a focal point in the plane (defined by the excitation light ray) of the sample. This has the advantage of being able to focus both the direct and reflected emission light on the same focal plane.

In another embodiment of the present invention, more than one kind of fluorescent tag may be used to image different biological structures of the sample.

A mixture of different kinds of fluorescent tag molecules is used to prepare the sample. Each kind of fluorescent tag attaches to different biological structures. The light emitted by the fluorescent tags may have a different frequency and the excitation light required to cause the tags to fluoresce may have a different frequency depending on the kind of fluorescent tag. Each tag may require its own set of excitation and emission filters selected for the excitation and emission light frequencies of the specific tag. The sample holder reflector is chosen to transmit or absorb all the excitation frequencies of the fluorescent tags while reflecting all the emission frequencies of the fluorescent tags.

The invention described herein is not to be limited in scope by the preferred embodiments herein described, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. For example, instead of transmitting the excitation light, the sample reflector may absorb the excitation light. Another example includes the use of a laser as the excitation light source. Since the laser produces essentially monochromatic light, using a laser as the excitation light source eliminates the need for an excitation filter. Such modifications are also intended to fall within the scope of the invention.

What is claimed is:

1. A microscope slide for increasing epifluorescent optical contrast of a fluorescently tagged sample emitting an emission light upon illumination by an excitation light, comprising:
   a top surface; and
   a bottom surface;
   a sample-proximal infrared reflecting film deposited on said top surface, wherein the infrared reflecting film at least partially reflects an infrared focusing light beam at or near a sample focal point or focal plane; and
   a dichroic reflecting film deposited on either said top surface, adjacent to, or in contact with, the sample, or said bottom surface, underneath the sample, wherein said dichroic reflecting film reflects the emission light emitted by said sample while transmitting the excitation light illuminating said sample.

2. The microscope slide of claim 1, wherein said sample comprises different fluorescent tag molecules selected for interacting with excitation light applied at a specific frequency to produce a specific frequency emission light, the specific frequency emission light being reflected by the dichroic reflecting film being suitable for reflecting said specific frequency light emitted from the fluorescent tags.

3. The microscope slide of claim 1, wherein said sample comprises more than one kind of fluorescent tag molecule for imaging different sample target, each target requiring a different dichroic reflecting film and excitation frequency.

4. The microscope slide of claim 1, wherein the one dichroic reflecting film is selected as capable to transmit or absorb all the different emission frequencies of the fluorescent tag molecules in the sample while reflecting all the emission frequencies of the fluorescent tags.

5. The microscope slide of claim 1 wherein different dichroic reflecting films may be utilized for the same sample containing different fluorescent tags molecules.

6. The microscope slide of claim 1, wherein the infrared reflecting film comprises a metal.

7. The microscope slide of claim 6 wherein the metal comprises titanium.

8. The microscope slide of claim 1 wherein the infrared reflecting film has a thickness of 0.6 nm to 90 nm.

9. The microscope slide of claim 1 wherein the infrared reflecting film reflects between 4 to 8% of an incident infrared beam.

10. The microscope slide of claim 9 wherein the infrared reflecting film reflects between 5.5 to 7% of the incident infrared beam.

11. The microscope slide of claim 1 wherein the infrared focusing light beam comprises a laser light of frequency in the infrared range.

12. The microscope slide of claim 1 which comprises a glass slide.

13. The microscope slide of claim 1 which is disposable.

* * * * *